(12) United States Patent  (10) Patent No.: US 9,119,735 B2
Accinni et al.  (45) Date of Patent: Sep. 1, 2015

(54) INTELLIGENT PROSTHETIC SOCKET SYSTEM WITH ACTIVE USER FEEDBACK INTERFACE AND REAL TIME PROSTHESIS DIAGNOSTICS

(75) Inventors: Clint Accinni, Littleton, CO (US); Michael L. Kaessner, Longmont, CO (US); Royce Heck, Highlands Ranch, CO (US)

(73) Assignee: 5280 Prosthetics LLC, Littleton, CO (US)

( * ) Notice: Subject to any disclaimer, the term of this patent is extended or adjusted under 35 U.S.C. 154(b) by 0 days.

(21) Appl. No.: 13/186,613

(22) Filed: Jul. 20, 2011

(65) Prior Publication Data

US 2012/0022667 A1  Jan. 26, 2012

Related U.S. Application Data

(60) Provisional application No. 61/366,012, filed on Jul. 20, 2010, provisional application No. 61/388,322, filed on Sep. 30, 2010.

(51) Int. Cl.
| | |
|---|---|
| *A61F 2/80* | (2006.01) |
| *A61B 5/00* | (2006.01) |
| *A61F 2/68* | (2006.01) |
| *A61F 2/54* | (2006.01) |
| *A61F 2/60* | (2006.01) |
| *A61F 2/70* | (2006.01) |
| *A61F 2/74* | (2006.01) |
| *A61F 2/76* | (2006.01) |

(52) U.S. Cl.
CPC .................. *A61F 2/80* (2013.01); *A61B 5/4851* (2013.01); *A61F 2/68* (2013.01); *A61F 2/54* (2013.01); *A61F 2/60* (2013.01); *A61F 2/70* (2013.01); *A61F 2002/689* (2013.01); *A61F 2002/705* (2013.01); *A61F 2002/707* (2013.01); *A61F 2002/747* (2013.01); *A61F 2002/763* (2013.01); *A61F 2002/764* (2013.01); *A61F 2002/765* (2013.01); *A61F 2002/769* (2013.01); *A61F 2002/7615* (2013.01); *A61F 2002/7625* (2013.01); *A61F 2002/7635* (2013.01); *A61F 2002/7665* (2013.01); *A61F 2002/802* (2013.01); *A61F 2002/805* (2013.01)

(58) Field of Classification Search
CPC ................ A61F 2/80; A61F 2002/802; A61F 2002/805; A61F 2002/807; A61F 2002/704; A61F 2002/48
USPC ..................................................... 623/33–37
See application file for complete search history.

(56) References Cited

U.S. PATENT DOCUMENTS

| | | | |
|---|---|---|---|
| 5,253,656 A | 10/1993 | Rincoe et al. | |
| 5,376,131 A | 12/1994 | Lenze et al. | |

(Continued)

*Primary Examiner* — Bruce E Snow
(74) *Attorney, Agent, or Firm* — Hogan Lovells US LLP

(57) ABSTRACT

An apparatus is provided for use with a prosthetic system. The apparatus includes a controller and a wireless smart device. The controller operates to gather data and derive prosthetic information from a plurality of sensors, and transmits the prosthetic information over a wireless radio link, where the controller and the plurality of sensors are disposed within a housing that is within the interior of a prosthetic socket, the prosthetic socket having a formed reservoir at a distal end inside of which the housing is disposed. The wireless smart device is coupled to the controller via the wireless radio link, and receives the prosthetic information, and provides visual and audio representations of the prosthetic information to a user.

42 Claims, 5 Drawing Sheets

(56) References Cited

U.S. PATENT DOCUMENTS

| | | |
|---|---|---|
| 5,485,402 A | 1/1996 | Smith et al. |
| 5,507,834 A | 4/1996 | Laghi |
| 5,549,709 A | 8/1996 | Caspers |
| 5,840,047 A | 11/1998 | Stedham |
| 5,904,722 A | 5/1999 | Caspers |
| 5,980,803 A | 11/1999 | Slemker et al. |
| 6,231,616 B1 | 5/2001 | Helmy |
| 6,231,617 B1 | 5/2001 | Fay |
| 6,273,918 B1 | 8/2001 | Yuhasz et al. |
| 6,287,345 B1 | 9/2001 | Slemker et al. |
| 6,500,210 B1 | 12/2002 | Sabolich et al. |
| 6,645,253 B2 | 11/2003 | Caspers |
| 6,679,920 B2 | 1/2004 | Biedermann et al. |
| 6,761,742 B2 | 7/2004 | Caspers |
| 7,025,792 B2 | 4/2006 | Collier |
| 7,033,400 B2 | 4/2006 | Currier |
| 7,150,762 B2 | 12/2006 | Caspers |
| 7,169,188 B2 | 1/2007 | Carstens |
| 7,275,218 B2 | 9/2007 | Petrella et al. |
| 7,427,297 B2 | 9/2008 | Patterson et al. |
| 7,468,079 B2 | 12/2008 | Collier |
| 7,632,315 B2 | 12/2009 | Egilsson |
| 7,655,049 B2 | 2/2010 | Phillips |
| 7,780,741 B2 | 8/2010 | Janusson et al. |
| 8,016,892 B2 * | 9/2011 | Colvin et al. ............ 623/24 |
| 2001/0005798 A1 | 6/2001 | Caspers |
| 2004/0030411 A1 | 2/2004 | Caspers |
| 2004/0167638 A1 | 8/2004 | Caspers |
| 2004/0260403 A1 | 12/2004 | Patterson et al. |
| 2005/0131550 A1 * | 6/2005 | Coop ............ 623/36 |
| 2005/0240282 A1 | 10/2005 | Rush et al. |
| 2007/0055383 A1 | 3/2007 | King |
| 2007/0168045 A1 | 7/2007 | Slemker et al. |
| 2007/0191965 A1 | 8/2007 | Colvin et al. |
| 2007/0213839 A1 | 9/2007 | Nachbar |
| 2007/0213840 A1 | 9/2007 | Townsend et al. |
| 2007/0255424 A1 | 11/2007 | Leydet et al. |
| 2008/0086218 A1 | 4/2008 | Egilsson |
| 2008/0140221 A1 | 6/2008 | Macomber et al. |
| 2008/0147202 A1 | 6/2008 | Danzig et al. |
| 2008/0221705 A1 | 9/2008 | Scussel |
| 2008/0243265 A1 | 10/2008 | Lanier |
| 2009/0030530 A1 | 1/2009 | Martin |
| 2009/0036998 A1 | 2/2009 | Finlinson et al. |
| 2009/0157196 A1 | 6/2009 | Danzig et al. |
| 2009/0237266 A1 | 9/2009 | Haynes et al. |
| 2010/0036455 A1 | 2/2010 | Sanders et al. |
| 2010/0131113 A1 | 5/2010 | Even-zohar |
| 2010/0191153 A1 | 7/2010 | Sanders et al. |
| 2011/0046748 A1 | 2/2011 | Martin et al. |
| 2011/0060421 A1 | 3/2011 | Martin et al. |
| 2011/0125291 A1 | 5/2011 | Tompkins et al. |
| 2011/0196510 A1 * | 8/2011 | Slemker et al. ............ 623/34 |

* cited by examiner

INTELLIGENT PROSTHETIC SOCKET SYSTEM WITH ACTIVE USER FEEDBACK INTERFACE AND REAL TIME PROSTHESIS DIAGNOSTICS

CROSS-REFERENCE TO RELATED APPLICATIONS

This application claims the benefit of the following U.S. Provisional Applications, each of which is herein incorporated by reference for all intents and purposes.

| SERIAL NUMBER | FILING DATE | TITLE |
| --- | --- | --- |
| 61/366,012 (AE.0103) | Jul. 20, 2010 | INTERNAL SOCKET MOUNTED PROSTHETIC VACUUM PUMP CONTROLLER AND DISPLAY |
| 61/388,322 (AE.0104) | Sep. 30, 2010 | INTELLIGENT PROSTHETIC SOCKET SYSTEM WITH ACTIVE USER FEEDBACK INTERFACE AND REAL TIME PROSTHESIS DIAGNOSTICS |

BACKGROUND OF THE INVENTION

1. Field of the Invention

This invention relates in general to the field of biomechatronics, and more particularly to a wireless intelligent prosthetic system having real time diagnostics and active user feedback.

2. Description of the Related Art

Prosthetics and prosthetic limbs have been used to replace human body since at least 1,000 B.C. Egyptian and Roman history is replete with recitations of wooden toes, iron hands and arms, wooden legs, feet and the like. However, it was not until the Renaissance that prosthetics began to provide for function (e.g., moving hands and feet) in addition to appearance. During this period the first prosthetic leg was developed having a suction socket that maintained a more effective and durable connection between a patient's residual limb and the leg.

Since that time, and particularly during the past 75 years, developments in the field of prosthetic devices have flourished in this country, particularly with the help of funding from the National Academy of Sciences, the Armed Services, the American Orthotics and Prosthetic Association, and other philanthropic entities. Beyond this country, The International Society for Prosthetics and Orthotics continues to foster both research and clinical practice worldwide.

In the 1980s, socket technology evolved from sockets made in the shape of a square bucket with no specialized adaptation to the specific size and shape requirements of the patient's residual limb to a socket that conformed to the patient's limb like a glove. With this advancement, patients were enabled to perform activities over and above simply walking—they were able to run, to walk both up and down stairs, and to step over substantially large objects. Today, amputees even compete in sports activities. And the pull on developers continues in this field as a result of these ever increasing needs.

Many patients are able to maintain a sufficient attachment of their limb to their prosthesis merely as a result of the good fit between a conforming socket and the limb, that is, gravity and friction do a good enough job of keeping the socket and prosthesis attached. However, there is a class of patients for whom maintaining an effective bond between limb and socket is a continual and ever evolving challenge. For some in this category, loss of "fit" is a result of changes in the size and shape of their residual limb. For others, the weight of the prosthesis relative to the residual limb precludes a good bond during activity. And for others, changes in their type of activity (e.g., running versus walking) cause the coupling between socket and limb to degrade.

It is for this class above that vacuum assisted devices and sockets have been more recently fielded. With a vacuum assisted prosthetic, the patient's limb is shielded with a protective cover such as a silicone liner over the top of which is placed a porous fabric sleeve, and the limb is inserted into a vacuum assisted socket. Through an air port in the socket, a vacuum pump is attached that is used to create a vacuum between the limb and the socket to enable the socket to be more effectively coupled to the limb. There are numerous developments in this field to include one-time external pumps, pumps that are carried by the patient, and pumps that are affixed to the exterior of the socket or to the prosthesis itself. Some pumps are manually operated. Other pumps are electronically activated either via a special activator (e.g. RF fob) or by control functions designed therein. Still other pumps provide a rudimentary form of automation that maintains a predetermined negative air pressure inside the socket cavity. Of these more advances pumps/controllers, some are able to gather limited data regarding wear which can be accessed through the use of special test equipment typically at a prosthetic specialist's facility. Most of the fit and wear data to date, however, is obtained through personal interview with the patient.

The present inventors have noted numerous limitations resulting from the state of the art including the requirement for special equipment requirements to both operate and access data captured by today's pumps/controllers. In addition, because these devices are either carried or mounted external to a prosthetic socket, additional manufacturing requirements are imposed on a socket (e.g., ports for connection of air hoses and electrical leads), and the pumps/controllers themselves are subject to damage due to their exposure to contaminants and unanticipated accidents. Furthermore, the present inventors have observed that the amount of data that is currently gathered by these devices is woefully lacking. As a result, the patient's prosthetic experience is problematic.

Accordingly, what is needed is an intelligent prosthetic socket system that can relay real time information to patients, where the information is derived from a series of sensors and data collection components.

Additionally, what is needed is a prosthetic socket system that includes an intelligent pump/controller that is disposed inside of a socket and that comprises a plurality of sensors for purposes of continually adjusting a vacuum between a residual limb and the socket.

Also what is needed is a prosthetic socket system including an intelligent pump/controller disposed inside of a prosthetic socket that gathers data related to fit and usage of an associated prosthesis.

Furthermore, what is needed is an intelligent pump/controller internal to a prosthetic socket that communicates information wirelessly to/from a commercially available "smart" device such as an IPHONE®, IPAD®, IPOD TOUCH®, or DROID®, where information from the smart device can be provided over the Internet for access by the user and authorized agents such as prosthetic fitters and medical personnel.

Moreover, what is needed is an intelligent pump/controller internal to a prosthetic socket that communicates information wirelessly to/from a multifunctional "smart" device that allows for a much broader and extensible set of controls and displays over that which has heretofore been provided.

SUMMARY OF THE INVENTION

The present invention, among other applications, is directed to solving the above-noted problems and addresses other problems, disadvantages, and limitations of the prior art. The present invention provides a superior technique for intelligently and automatically operating a prosthetic system over periods of time, both short term and long term. In one embodiment, an apparatus is provided for use with a prosthetic system. The apparatus includes a controller and a wireless smart device. The controller operates to gather data and derive prosthetic information from a plurality of sensors, and transmits the prosthetic information over a wireless radio link, where the controller and the plurality of sensors are disposed within a housing that is within the interior of a prosthetic socket, the prosthetic socket having a formed reservoir at a distal end inside of which the housing is disposed. The wireless smart device is coupled to the controller via the wireless radio link, and receives the prosthetic information, and provides visual and audio representations of the prosthetic information to a user.

One aspect of the present invention contemplates an apparatus for use with a prosthetic system. The apparatus includes a housing and a wireless smart device. The housing is within the interior of a prosthetic socket, the prosthetic socket having a formed reservoir at a distal end inside of which the housing is disposed. The housing has a controller and a seal. The controller operates to gather data and derive prosthetic information from a plurality of sensors, and transmits the prosthetic information over a wireless radio link. The seal seals the housing to the interior of the prosthetic socket, and seals a low pressure side within the prosthetic socket from an ambient environment. The wireless smart device is coupled to the controller via the wireless radio link, and receives the prosthetic information, and provides visual and audio representations of the prosthetic information to a user.

Another aspect of the present invention comprehends an apparatus for use with a prosthetic system. The apparatus includes a prosthetic socket, a housing, and a wireless smart device. The prosthetic socket provides a conforming receptacle for a residual limb of a user, the prosthetic socket having a formed reservoir at a distal end. The housing is disposed in said reservoir of the prosthetic socket. The housing includes a controller and a seal. The controller gathers data and derives prosthetic information from a plurality of sensors, and transmits the prosthetic information over a wireless radio link, where the controller and the plurality of sensors are disposed within the interior of the housing. The seal seals the housing to the interior of the prosthetic socket, and seals the interior of the prosthetic socket from an ambient environment. The wireless smart device is coupled to the controller via the wireless radio link, and receives the prosthetic information, and provides visual and audio representations of the prosthetic information to the user.

BRIEF DESCRIPTION OF THE DRAWINGS

These and other objects, features, and advantages of the present invention will become better understood with regard to the following description, and accompanying drawings where.

DETAILED DESCRIPTION

The following description is presented to enable one of ordinary skill in the art to make and use the present invention as provided within the context of a particular application and its requirements. Various modifications to the preferred embodiment will, however, be apparent to one skilled in the art, and the general principles defined herein may be applied to other embodiments. Therefore, the present invention is not intended to be limited to the particular embodiments shown and described herein, but is to be accorded the widest scope consistent with the principles and novel features herein disclosed.

Figure 1:
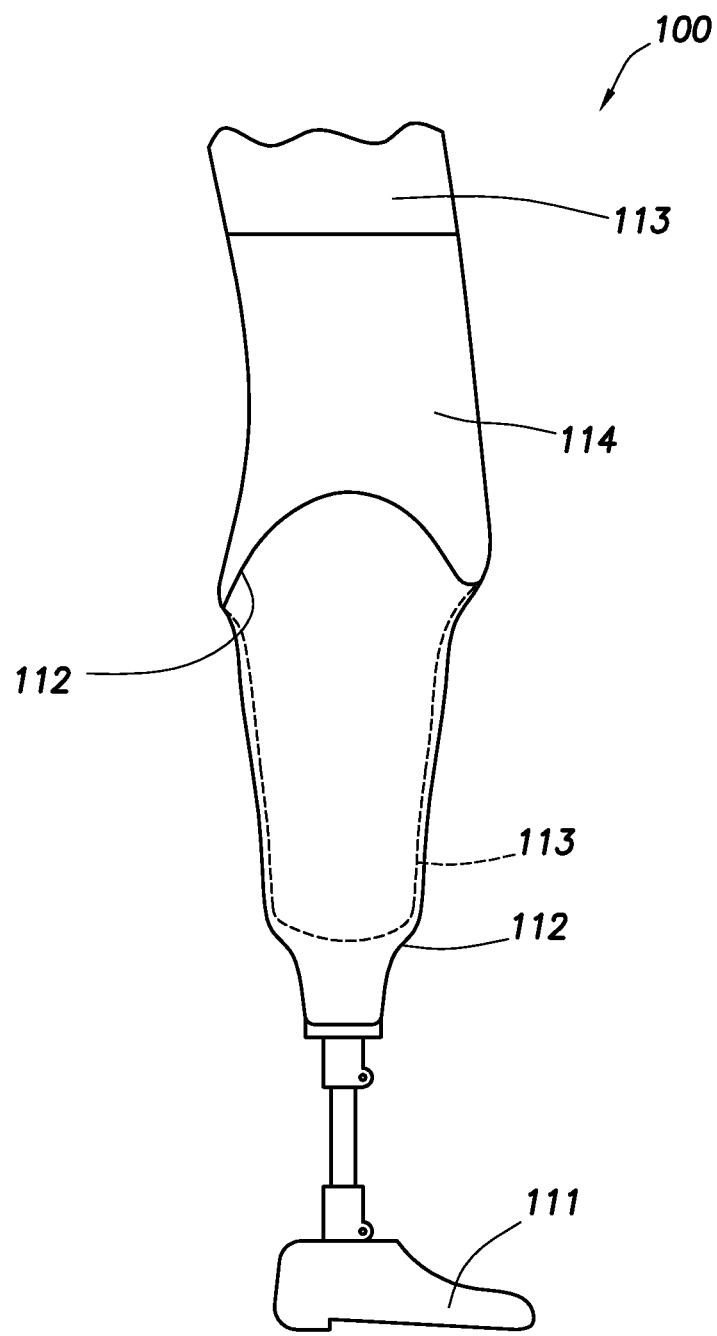
FIG. 1 is a diagram illustrating a present day approach to attaching and securing a prosthetic device to a residual patient limb.

In view of the above background discussion on present day prosthetic devices and associated techniques employed within the field to reliably and effectively provide for adequate sealing and patient comfort, a discussion of present day approaches for maintaining a seal between a prosthetic device (e.g., a prosthetic leg) and a patient's residual limb will be presented with reference to FIG. 1. Following this, a discussion of the present invention will be presented with reference to FIGS. 2-5. The present invention overcomes the numerous limitations and disadvantages of present day prosthetic devices by providing fully enclosed wireless apparatus that enables real-time analysis and control of patient and prosthetic operating parameters via a wireless device interface.

Turning to FIG. 1, a diagram is presented illustrating a present day approach 100 for attaching and securing a prosthetic device 111 to a residual limb 113 of a patient. As one skilled in the art will appreciate, prosthetic devices 100 are myriad in the art and are predominately comprised of artificial limbs such as legs and arms, but may also include subsets of these appendages to include feet and hands. In order to teach limitations of the art along with disclosure of the present invention, the example of a combination prosthetic leg and foot will be employed, however it is noted that the scope of the present invention is not to be restricted to this example as the apparatus and principles of operation extend to all such prosthetic devices. In addition, henceforth a patient having a residual limb to which a prosthetic device is attached will be referred to as a "user" and the entire system of apparatus comprising the prosthetic device (i.e., limb, structural components, socket, housing, covers, etc.) will be referred to as a "prosthetic system" 100.

Accordingly, the system 100 includes an artificial foot 111 (including vertical structural components) fabricated from and by any of a number of well known materials and processes. A socket 112 is coupled to the foot 111 and a user's residual limb 113 is inserted into the socket 112. In many cases, gravity and friction alone are all that are needed to adequately secure the limb 113 to the system 100. However, as one skilled in the art will appreciate, there are cases where the above coupling methods are insufficient, such as when a prosthesis 100 weighs much more than the residual limb, or when a prosthetic leg 100 is employed under more stringent operating conditions (e.g., a racing prosthesis). In these cases it is customary to provide a vacuum seal to affect a seal such that the prosthetic system 100 stays attached to the residual limb 113. FIG. 1 shows one mechanism where vacuum techniques are employed to maintain a seal between the residual limb 113 and the prosthesis 100.

In a vacuum assisted prosthesis 100, typically the residual limb 113 is covered with a silicone sleeve (not shown) to protect the limb 113 from effects of the vacuum. While it is advantageous that a lower air pressure around the limb 113 that that of the ambient atmosphere has the advantage of drawing blood and fluids into the limb 113, one skilled will also appreciate that too much negative pressure will cause damage to the limb 113.

The sleeve is then covered with a sock (not shown) made of porous fabric such as cotton, polyester blend, or the like to allow for air movement. Thus, the covered limb 113 is inserted into a socket 112, to which the foot 111 is mechanically attached. The attachment techniques vary, but generally the socket 112 is secured to the foot 111 by bolts that are threaded into inserts (not shown) at the top of the foot structure 111. The socket 112 is typically thermoplastic or laminated shell that is formed to comport with the shape of the residual limb 113. The socket 112 is then covered by a rubber sleeve 114 that at the top end secures the sleeve 114 to the covered limb 113 and at the bottom secures the sleeve 114 to the socket 112. A vacuum is created within to secure the sleeve 114 to the covered limb 113 and to secure the sleeve 114 to the socket 112.

There are many known methods of drawing air from the inside of the socket 112 to the outside of the socket 112 to create the level of negative internal pressure necessary to secure the socket 112 to the limb 113, but the present inventors have noted that all of these methods involve a pump (not shown) that is external to the socket 112. This pump may be attached to the socket 112 or it may be freestanding. It may be fully mechanical and operated by the change in angle between the artificial foot 111 and the piston, or it may be an electrical pump mounted on the system 100. Other variations include an electrical pump mounted inside the socket 112 with an electronic controller mounted on the artificial leg/foot 111. Regardless of the configuration, the present inventors have noted that present day mechanisms as described above all require user intervention to adjust the vacuum setting based on anticipated activity. It is noted that in the case of a mechanical pump, many users are heavy enough to actuate the pumping mechanism and these types of devices provide not way to regulate internal air pressure.

In many of the above configurations, access to the interior of the socket 112 is generally gained through a port (not shown) on the socket itself. Thus, the user accesses the pump at a fixed location, or carries the pump, or the pump is secured to the socket 112 or to the foot 112, and an air hose and electrical leads (if required) couple the pump to the socket 112. The present inventors have observed that having a pump at a fixed location is disadvantageous because vacuum leaks most often occur during use, which may not be at the fixed location. In addition, an external pump increases the risk of damage to the pump during use and render the prosthesis more visually obvious.

Known pumping apparatus also includes special purpose electro-mechanical devices that most often include external sensors and wires—piercing the wall of the socket 112 and creating a point for potential vacuum leak—coupling a pump thereto, and these devices can only be accessed via special purpose equipment that most often is not available to the user. That is, the user must travel to a designated location in order to communicate device usage and wear information to the special purpose equipment. Accordingly, information analysis is not performed in real time. More often, most of the information needed to adjust the prosthetic device 111 and socket 112 for fit and performance is obtained through a personal interview with the patient. In the case of a more capable pumping device, the information is obtained by coupling the special purpose equipment to the device at a manufacturer representative's site either via wired or wireless connection. The present inventors have noted that requiring an access port on the wall of the socket 112 increases the cost of manufacturing, and overall cost to the user since sockets are frequently replaced resulting from wear and fit issues. In addition, present day devices provide very limited information on the operation of the vacuum setting. Consequently, a prosthetic fitter must estimate the level of vacuum setting that may be required for each user. In terms of control, some electrical pumps have control switches mounted thereon or are actuated by a custom wireless RF fob.

In addition, any real-time information that is obtained by present day pumping devices is communicated to the user via very rudimentary and user-unfriendly mechanisms, such as coded audio or visual signals. Some devices include prosthetic controllers that when coupled to the special purpose equipment are capable of affecting a small range of control settings (e.g., vacuum level). The user may be able to turn the pump on and off or it may work automatically to provide a predetermined level of vacuum.

The present inventors have observed that there are available systems that gather data and that perform rudimentary prosthetic user alerts as described above. However, all of these systems have pumping devices that are not part of the prosthetic socket 112. The majority of the designs include numerous wires and sensors that have to be ported inside the prosthetic socket 112 with a monitoring device that is external to the socket 112. In addition, these prosthetic systems 100 are not portable (i.e., they are not reusable when a socket 112 is replaced), and they are difficult to fabricate. No existing device has a real time dialog with the user other than simple audio and visual alerts. The present inventors have also observed that there is no prosthetic system 100 today which is portable, which operates in real time, and which is capable of communicating to the user in an ongoing dialog instructions for operation or indications of misfit or malfunction. Consequently, users are constrained to accept the type of fit and comfort that these systems 100 are capable of providing.

For the above reasons, and others, the present inventors have noted a need in the art for an intelligent prosthetic system that gathers and analyzes data in real time, and that affects an ongoing two-way dialog with a user for purposes of awareness and control. The present inventors have also determined a need for the intelligent prosthetic system to be fabricated such that the pump itself and all sensors are internal to a socket 112 in order to preclude potential vacuum leaks. And there is a need for such an intelligent pumping apparatus having sensing and control components therein to communicate wirelessly to the user via commercially available and cost effective mechanisms, and that do not require additional control devices (e.g. a special fob) beyond what is normally carried by the user. The present inventors have further noted that it is desirable for such a prosthetic system to include mechanisms for reuse when the user swaps out a socket 112. The present inventors have moreover observed that it is desirable to provide for easy upgrade of functionality of the prosthetic system 100 without a requirement to disassemble major components.

The present invention overcomes the limitations alluded to above and furthermore achieves each of the preceding objectives through a combination of smart-device wireless technologies and a programmed intelligent internal pump and control apparatus. In one embodiment, the present invention comprises a microprocessor controlled socket coupled to a smart device (e.g., smart phone, IPHONE®, IPAD®, ANDROID® phone, WINDOWS®-based phone, personal digital assistant (PDA), or like devices) for user feedback and prosthetic socket adjustments. Hereinafter, these types of devices will be referred to as a smart device. It is through the use of an every day smart device that all of these control options and intelligent socket features become possible and useable. Previous developments in the art have not incorporated a smart device, thus the only time the data could be adjusted or gathered was to connect the a prosthetic system to a computer and download information. The present invention provides the advantage of using a single component with multiple sensors and an on board central processing unit (CPU), microprocessor, or microcontroller housed inside the prosthesis, and wirelessly coupled to display screens and functions available in the smart device. In addition, the use of a smart device allows the data to be transmitted in real time via the Internet to a prosthetic fitter who is monitoring fit and use.

The present invention furthermore provides for a real-time prosthetic user feedback system coupled to a computer controlled system that derives information from a multitude of sensors and other elements to relay information to the user. A control module according to the present invention reports information to the user via the smart device through clear concise written messages and warnings. User information will include internal socket conditions including, but not limited to temperature, vacuum level, moisture, movement, pressure, and external socket conditions including, but not limited to, angle indications, altitude, Global Positioning System (GPS) parameters, accelerometer parameters, force information, gyroscopic information, camera information, memory card information, and timer/clock values. The controller according to the present invention monitors and adjusts socket conditions through bladder systems, temperature control systems, suspension control mechanisms, and etc.

The present invention moreover provides for understandable communication with the user. The communication provides for written or verbal instructions to user, in contrast to present day beep and vibratory alarms, by real-time data and exact instructions for what to do with the prosthesis. For example, the device according to the present invention will inform prosthetic users when to add a prosthetic sock (a way of tightening the prosthetic system), when to remove a sock because there is not enough distal contact, when to change a fabric liner because there is too much moisture, when to service the prosthesis or parts of the prosthesis. The device according to the present invention will advise the user to adjust pressure because of a change in altitude, it will provide pedometer information (e.g., steps walked, feet climbed, cadence, speed). The device will record and provide the time the prosthesis has been worn, and display and guide the user through a wearing schedule. The present invention will advise the user if abnormal movement is detected (e.g., pistoning), and it will record data on prosthetic wear, suspension effectiveness, and compliance to the user schedule. The device will also be able to store and display all of the pertinent information about the prosthesis (e.g., foot, size, category, patient weight, date fit, knee unit, knee settings, socket design, liner type, suspension type, etc.) An alternative embodiment additionally provides for a clinical data section to help with medical justifications, and to provide pertinent clinical data for prosthetists to analyze data and resolve fit issues.

In a further embodiment, the data system is connected to other systems that control bladder systems, vacuum systems, fluid control systems, temperature control systems, emergency systems, suspension systems, mechanical and electrical alignment/gait control systems automatically based on the information collected and derived from the on board socket control and feed back system.

Advantageously, the system according to the present invention is modular—a removable and reusable unit—that is, in one embodiment disposed inside a prosthetic socket with sensors and diagnostic tools to relay information to prosthetic users. Many prosthetic users have insensate residual limbs (i.e., no feeling) and they are unable to detect when to check their limb for pressure. Some users cannot remember how long to wear the limb. When to add and remove socks is also a big problem for many users. Often times suspension is no longer adequate and users cannot detect micro movement in a prosthesis. Every prosthesis requires service; many patients forget to have regular service checks performed. The present invention overcomes these limitations by providing a mechanism that can determine if any of the aforementioned circumstances have transpired and will communicate this with the user wirelessly via a conventional smart device. The present invention will now be discussed with reference to FIGS. 2-5.

Figure 2:
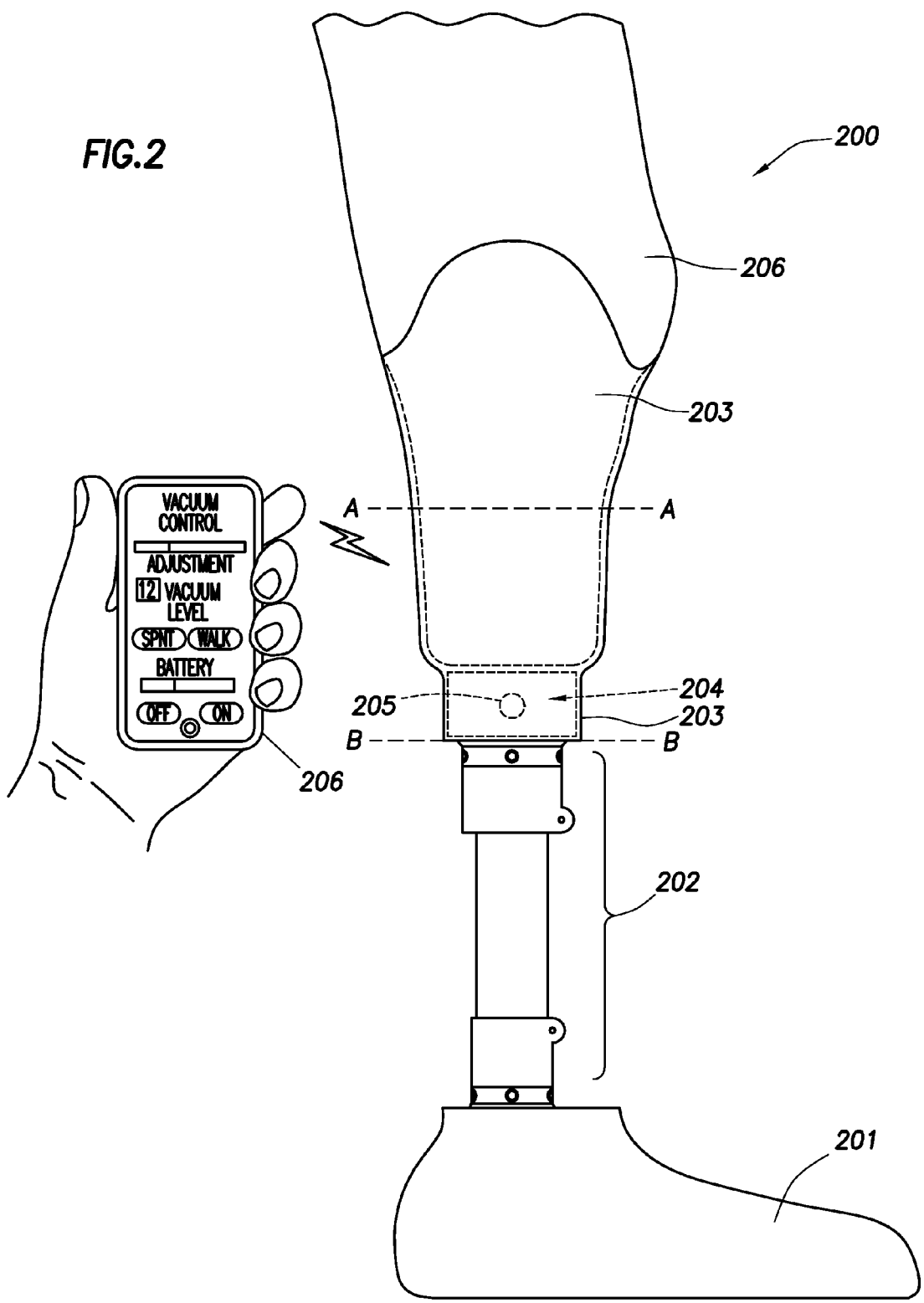
FIG. 2 is a diagram depicting a side view of an intelligent prosthetic system according to the present invention.

Turning to FIG. 2, a diagram 200 is presenting depicting a side view of an intelligent prosthetic system according to the present invention. The system includes a prosthetic socket 203 having extra volume at the distal end into which a smart device 204 is placed. Hereinafter, the smart device 204 may be referred to as a "puck" 204 due to its resemblance to a hockey puck. The puck 204, among other features, includes, in one embodiment, a CPU, memory, power supply, a wireless interface, and a plurality of sensors. In one embodiment, the power supply comprises a rechargeable battery that is accessed for charging via a port on the top of the puck. Another embodiment contemplates an inductively charged battery that is recharged in proximity to an inductive recharging pad. One embodiment considers an application program disposed within the memory that provides for one or more of the functional features disclosed above. Alternative embodiments contemplate one or more of the following sensors coupled to the CPU and disposed within the puck 204: accelerometer, GPS sensor, barometric pressure sensor, and temperature sensor. Other embodiments envisage one or more of the sensors disposed external to the puck 204, situated within the socket 203, and coupled to the CPU through sealed access points in the cover of the puck 204.

The puck 204 also includes a vacuum pump that is controlled by the CPU. The vacuum pump has an intake port that is coupled to a low pressure port on the top of the puck 204 and an exhaust port that is coupled to an exhaust port on the bottom of the puck 204. The application program executes on the CPU to affect control of the pump in accordance with programmed parameters and data that is read by the sensors. One embodiment of the puck 204 includes an airtight and watertight seal that seals the puck 204 to the socket 203 so that an appropriate vacuum can be established on the intake side of the puck 204 and air can be discharge via the exhaust side of the puck, typically into a vertical structure 202 that forming a hollow leg portion of a combination leg and foot prosthesis. In one embodiment a prosthetic foot 201 is coupled to the vertical structure 202. The socket 203, vertical structure 202, and foot 201 are all fabricated by known means, as alluded to above. As noted above, other embodiments of the present invention include such a system configured as a prosthetic arm/hand combination, a prosthetic foot, and a prosthetic hand. A residual limb 206 is inserted into the socket 203 as described above and the system is configured to maintain a seal between the residual limb 206 and the socket 203 such that the system stays coupled to the limb 206.

In one embodiment, programming of the puck 204 provides for default levels of vacuum inside the socket and the air pressure within the socket is automatically maintained in accordance with data read through the sensors. The puck 204 communicates wirelessly with a smart device 206 for purposes of providing information and alerts to a user, as has been described above. In another embodiment, the user may additionally employ touch controls on the smart device 206 to override the predetermined air pressure levels. That is, the user can take control of the pump via the smart device 206. In addition, the user may indicate via the smart device 206 that a different operating mode is to be employed, such as sprinting versus walking, which requires a different pressure level to maintain a good seal in the socket.

The puck 204 optionally includes a manual switch 205 to allow the user to operate the pump in the absence of the smart device 206 or in the event that the smart device 206 fails. One embodiment of the switch contemplates a sealed push-on/push-off (momentary contact) switch that is sensed by the CPU. Another embodiment envisages a Hall effect switch disposed internally in the puck 204, where the Hall Effect switch is activated by a magnetic device (e.g., a wand) having a level of magnetic flux that is adequate to actuate the switch when held in proximity thereto. The present inventors note that according to the present invention no vacuum inlet on the socket 203 is required, in contrast to that which has been provided heretofore.

Figure 3:
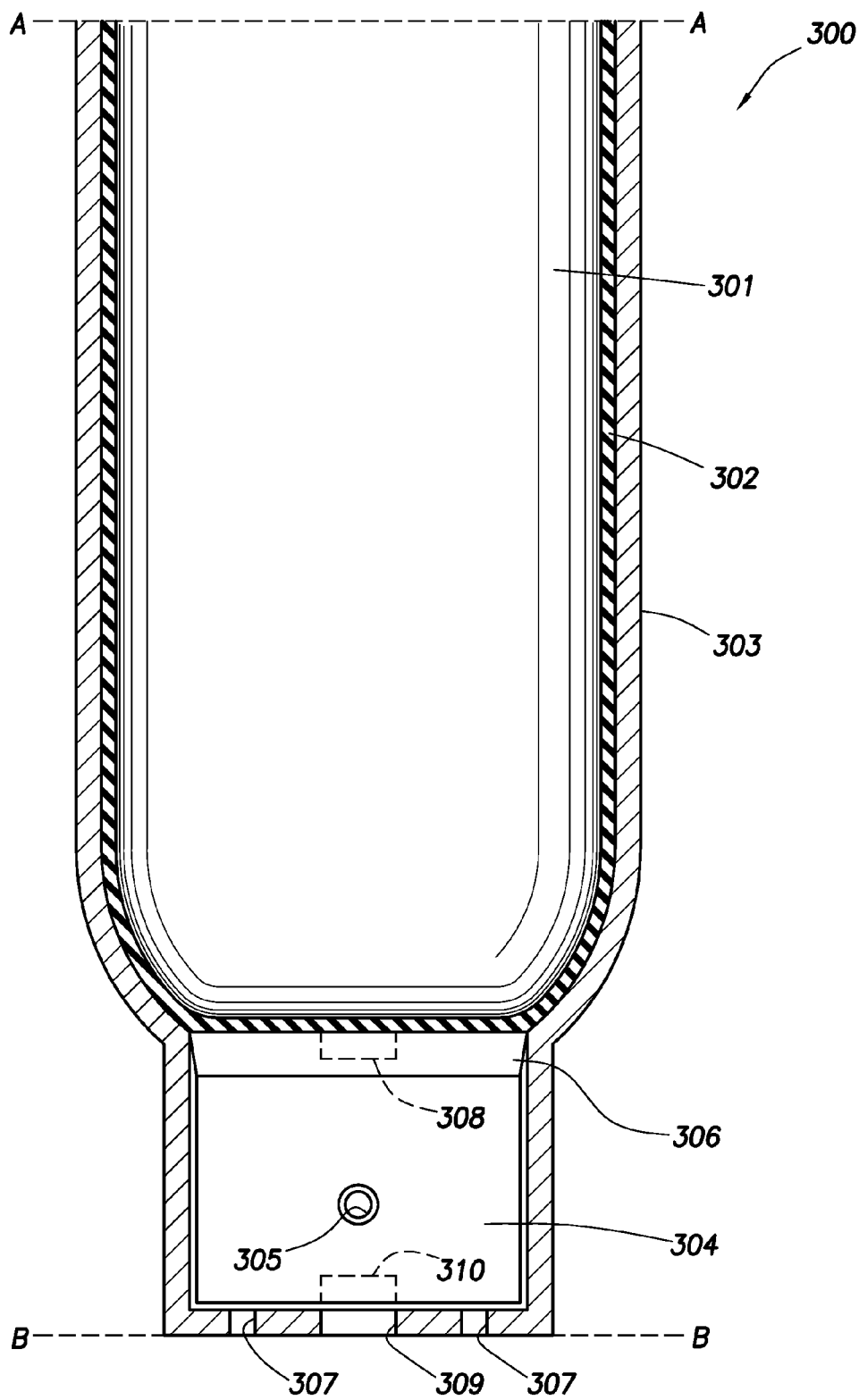
FIG. 3 is a diagram featuring a cross-sectional view of the intelligent prosthetic system of FIG. 2 taken from line A-A to line B-B.

Now referring to FIG. 3, a diagram 300 is presented featuring a cross-sectional view of the intelligent prosthetic system of FIG. 2 taken from line A-A to line B-B. The diagram 300 shows a silicone liner 301 that covers a residual limb. The liner 301 is covered with a porous fabric sleeve 302 which is inserted into a socket 303 according to the present invention. The socket 303 has a formed reservoir at its distal end in which a puck 304 according to the present invention is disposed. The puck has a primary seal 306 that contacts with the socket to form a seal separating a low pressure side of the system (i.e., the side adjacent to the fabric sleeve 303) form a high pressure side of the system. The puck 304 includes an intake port 308 on the low pressure side and an exhaust port 310 on the high pressure side. The puck 304 includes threaded receptacles where bolts are inserted through holes 307 in the distal end of the socket 303. An exhaust hole 309 is also provided in the socket 303 through which air is discharged from the exhaust port 310. As noted earlier, the puck 304 may include an override control switch 305.

In operation, a controller (not shown) within the puck 304 is programmed to execute one or more of the above noted functions and to communicated wirelessly with a smart device to maintain an effective vacuum seal between the limb and the socket 303 under varied use conditions.

Figure 4A:
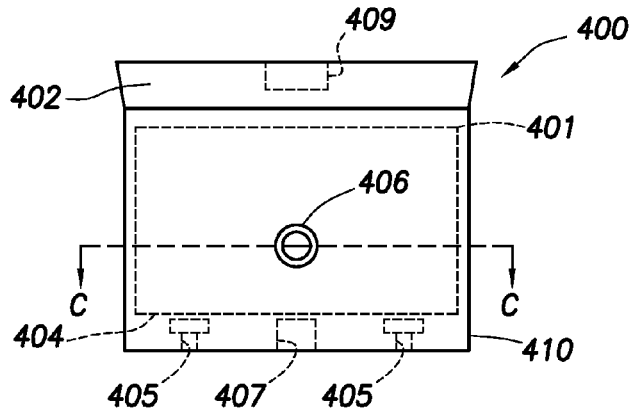
FIG. 4A is a detailed side view of an intelligent puck 400 according to the present invention, as may be employed in the prosthetic system of FIGS. 2 and 3.

Turning now to FIG. 4A, a diagram is presented showing a detailed side view of an intelligent puck 400 according to the present invention, as may be employed in the prosthetic system of FIGS. 2 and 3. The puck 400 comprises a cylindrical housing 410 having a top and a bottom. In one embodiment the housing 410 is fabricated aluminum and the bottom has four threaded receptacles 405 for mounting bolts that pass through holes in the distal end of a socket according to the present invention, and which attach the socket to a vertical prosthesis structure. Other embodiments contemplate a housing 410 fabricated from any material (e.g., plastic) strong enough for the application. The bottom of the housing 410 also has an exhaust port 407 that is coupled to a high pressure side of a pump internal to the housing 410. The top of the housing 410 has an inlet port 409 that is coupled to a low pressure side of the pump. Around the top of the housing a primary seal 402 is disposed that seals the puck 400 to the socket. An optional switch 406, as described above, may be present on the side of the housing. In one embodiment, the puck housing 410 itself (i.e., no internal components) can be effectively employed as a modular negative pressure tank that seal the distal aspect of a conforming socket.

In one embodiment, components as described above (e.g., power supply, CPU, memory, sensors) may be disposed on a printed circuit board 401 having electrical and pneumatic leads that couple components on the board 401 to the switch 406, a charging port 408, pressure ports 409, 407, and any sensors (not shown) external to the housing 410.

Figure 4B:
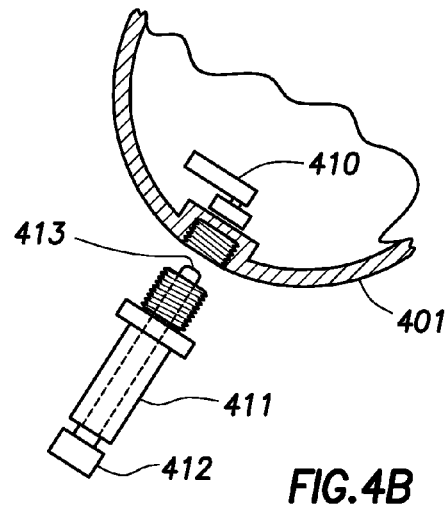
FIG. 4B is a diagram illustrating a top cross-sectional view of the puck of FIG. 4A taken at line C-C.

FIG. 4B is a diagram illustrating a top cross-sectional view of the puck 400 of FIG. 4A taken at line C-C. The diagram shows how a sealed momentary switch 411 a having cap 412, an actuator 413, and internal contacts 410 may optionally be configured on the housing 401. As noted above, a Hall Effect switch may be mounted internal to the housing, precluding the need to modify the housing 410 or the socket for external actuation.

Figure 4C:
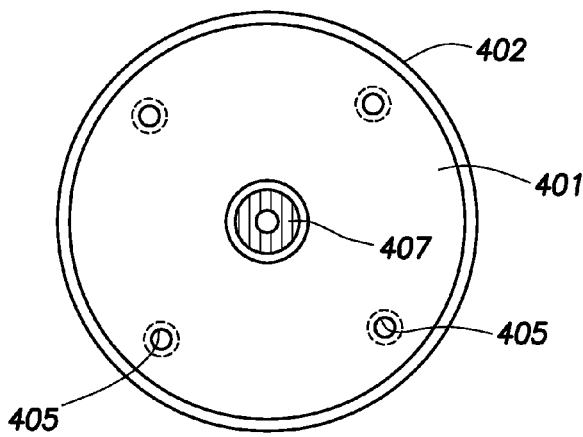
FIG. 4C is a diagram detailing a bottom view of the puck of FIG. 4A.

FIG. 4C is a diagram detailing a bottom view of the puck of FIG. 4A. A high pressure side port 407 is provided at center of the bottom with four threaded holes 405 spaced around the port 407 to provide for attachment of the socket to vertical structure members of the prosthesis. The primary seal 402 surrounds the top of the puck 400. As noted above, air is discharged by the pump through the exhaust port 407 and into the structure members.

Figure 4D:
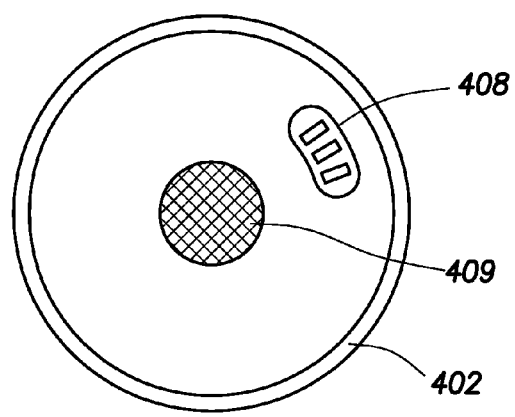
FIG. 4D is a diagram showing a top view of the puck of FIG. 4A.

FIG. 4D is a diagram showing a top view of the puck of FIG. 4A. The primary seal 402 surrounds the top of the puck 400 and a vacuum inlet port 409 is disposed in the center of the top. In one embodiment, the inlet port 409 comprises a waterproof filter. Additionally, a charge port 408 is disposed on the bottom of the puck to allow a charging device to be coupled to the battery. One embodiment of the present invention contemplates a socket having a hole around the charge port 408 to allow the puck 400 to plug in to a charging device.

Figure 5:
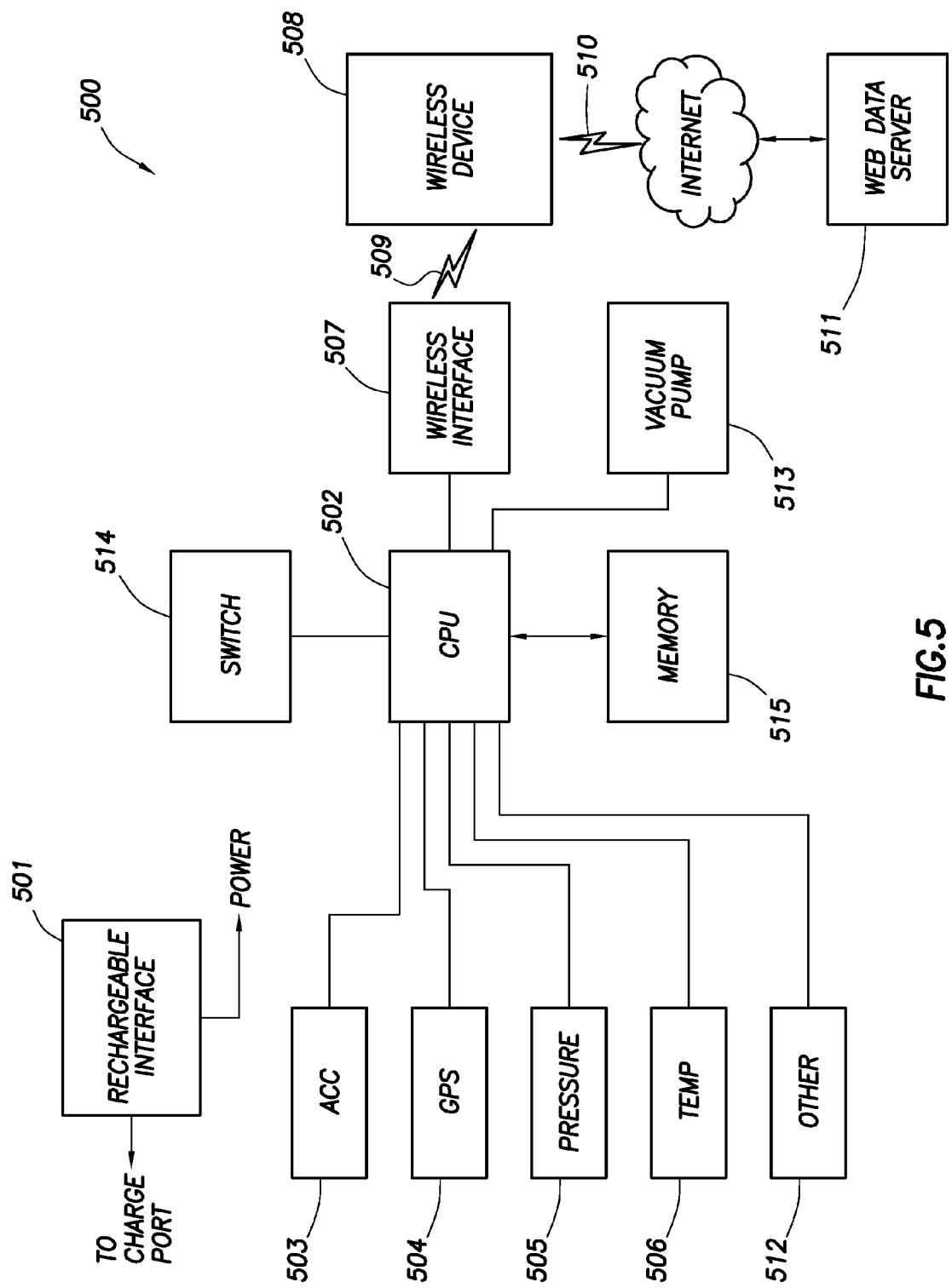
FIG. 5 is a block diagram of a puck controller according to the present invention.

FIG. 5 is a block diagram of a puck controller 500 according to the present invention. Elements of the controller 500 may be disposed on the circuit board 401 of FIG. 4A. The controller 500 includes a power supply 501 that provides power to the controller 500. In one embodiment the power supply 501 comprises a rechargeable battery. The supply 501 is coupled to the charge port 408. The controller 500 includes a CPU 502 that is coupled to an override switch 514 as described above, and to a memory 515. In one embodiment, the memory 515 comprises flash read-only memory (ROM) and the CPU 502 includes random access memory (RAM). Another embodiment contemplates that the memory 515 comprises a combination of any well known ROM and RAM. An application program providing for the functions disclosed herein is stored in the ROM portion of the memory 515. Sensors that may be coupled to the CPU 502 include an accelerometer 503, a GPS receiver 504, a barometric pressure sensor 505, a temperature sensor 506, and any other type of sensor 512 that may be employed to perform additional functions as programmed into the application program. For example, sensor 512 may comprise a strain gauge that is mounted on the top of the puck to detect excess limb pressure. Another embodiment contemplates sensor 512 comprising one or more gyroscopes to provide gyroscopic information. Accordingly the application program will execute so that the user is informed on the smart device that the limb is seated to low in the socket.

A wireless interface 507 is also coupled to the CPU. In one embodiment, the wireless interface 507 comprises a BLUETOOTH® transceiver. Another embodiment contemplates an IEEE 802.11 transceiver. The wireless interface 507 is employed by the CPU to communicate with a wireless smart device 508 via a wireless link 509. A device application program (not shown) resides within the smart device 508 to provide for smart device functions as described above.

A vacuum pump 513 as described above is also coupled to the CPU and is controlled by the CPU.

Optionally, the wireless device 508 is coupled to the Internet via any of a number of well known wireless links 510, which provides connection to a web data server 511 for purposes of device monitoring.

Operationally, the application program in the memory 515 and its counterpart in the smart device 508 operate to control functions of the smart prosthesis system as described above by reading and analyzing data from the sensors 503, 504, 505, 506, 512, and the switch 514. Accordingly, the CPU 502 actuates the vacuum pump 513 to maintain an effective seal between the limb and the socket under conditions directed by the user through use of the smart device 508.

One advantage of the present invention is that a modular design embodiment of the puck having pump and all sensors located therein enables a socket fabricator to easily move the puck from an older socket to a newer socket. Another benefit of the present invention is that multiple sensors are provided to allow for more precise automatic vacuum level adjustments that adapt to a user's change in activity level.

The present invention additionally provides a mechanism for displaying and controlling many more parameters regarding fit and function of prosthetic members than which enables a prosthetic device manufacturer to provide a better and more comfortable fit for the user.

An additional benefit provided by the present invention is that the user is not required to carry extra pump control devices such as an RF fob. Complete control of the prosthetic system is achieved through a smart device which most user's now carry on their person.

Because of the design of the puck according to the present invention, all holes heretofore required in the socket for hoses or electrical leads have been eliminated.

Many prosthetic sockets have a distal attachment plate. Since one embodiment of the present invention provides an aluminum puck housing that mounts the socket to vertical structural members, a requirement to provide the distal attachment plate is removed, thus reducing the cost of a prosthetic socket. And because all controller and pumping hardware is mounted internal to the socket, these elements are subject to impact damage. There are no hoses and wires to be snagged and damaged. The elements are protected from foreign object ingestion.

Mounting the pump inside of a socket reduces the noise level of the device when pumping, resulting in a more socially comfortable environment for the user and those nearby.

Because the present invention utilizes existing smart devices such as an IPHONE, IPAD, ANDROID phone, or the like, application software disposed therein can be upgraded easily by the users under current processes provided for by companies such as APPLE COMPUTER® and GOOGLE®. In addition, the application software/firmware within the puck controller can be automatically updated remotely.

Because the present invention provides for connectivity to the Internet, data collected for a particular system can be easily accessed by other entities such as medical and emergency personnel, insurance companies, and other prosthetic fitters.

Because of the virtually unlimited memory provided by connectivity to a web data server, the present invention provides long term collection and analysis of activity and wear parameters that enhance medical record keeping, training, and progress tracking, Although the present invention and its objects, features, and advantages have been described in detail, other embodiments are encompassed by the invention as well. For example, although the present invention has been discussed predominately in terms of a puck having a vacuum pump, a controller, and multiple sensors disposed therein, other embodiments are contemplated to include adaptations of the modular puck housing to provide for alternative prosthetic suspension mechanisms. In one embodiment, the top portion of the housing is removed and replaced with apparatus such as, but not limited to, pin locks, lanyards, suction, expulsion valves, magnetic locks, or a negative pressure reservoir.

Those skilled in the art should appreciate that they can readily use the disclosed conception and specific embodiments as a basis for designing or modifying other structures for carrying out the same purposes of the present invention, and that various changes, substitutions and alterations can be made herein without departing from the scope of the invention as defined by the appended claims.

What is claimed is:

1. An apparatus for use with a prosthetic system, the apparatus comprising:

a controller, that operates to gather data and derive prosthetic information from a plurality of sensors, and that transmits said prosthetic information over a wireless radio link, wherein said controller and said plurality of sensors are disposed within a housing that is completely and entirely disposed within an interior cavity of a prosthetic socket that provides also for insertion of a covered residual limb into said interior cavity, said prosthetic socket having a formed reservoir within said interior cavity inside of which said housing is disposed, and wherein said housing presents a first surface for contacting a second surface of said covered residual limb when inserted into said interior cavity;

a pump, wherein the pump is coupled to said controller and wherein the pump is operable to maintain a prescribed negative air pressure within said prosthetic socket, and wherein the pump is disposed within the housing; and a wireless smart device, coupled to said controller via said wireless radio link, that receives said prosthetic information, and that provides visual and audio representations of said prosthetic information to a user.

2. The apparatus as recited in claim 1, wherein said plurality of sensors comprises:

an accelerometer, that senses relative motion data corresponding to the prosthetic system, and that provides said relative motion data to said controller, wherein said controller derives a portion of said prosthetic information based upon said relative motion data.

3. The apparatus as recited in claim 1, wherein said plurality of sensors comprises:

a Global Positioning System (GPS) receiver, that senses real time position data corresponding to the prosthetic system, and that provides said real time position data to said controller, wherein said controller derives a portion of said prosthetic information based upon said real time position data.

4. The apparatus as recited in claim 1, wherein said plurality of sensors comprises:
a temperature sensor, that senses temperature data corresponding to the prosthetic system, and that provides said temperature data to said controller, wherein said controller derives a portion of said prosthetic information based upon said temperature data.

5. The apparatus as recited in claim 1, wherein said plurality of sensors comprises:
a barometric pressure sensor, that senses pressure data corresponding to the interior of said prosthetic socket, and that provides said pressure data to said controller, wherein said controller derives a portion of said prosthetic information based upon said temperature data, and wherein said vacuum pump is actuated additionally as a function of said pressure data.

6. The apparatus as recited in claim 1, wherein said wireless radio link comprises a BLUETOOTH radio link, and wherein said smart device comprises a smart cellular telephone.

7. The apparatus as recited in claim 6, wherein said smart cellular telephone executes an application program that enables said smart cellular telephone to receive and transmit said prosthetic information, to provide said visual and audio representations, and to receive input from said user for transmission to said controller.

8. The apparatus as recited in claim 7, wherein said visual and audio representations indicate time of wear for the prosthetic system.

9. The apparatus as recited in claim 7, wherein said visual and audio representations indicate a time to remove the prosthetic system.

10. The apparatus as recited in claim 7, wherein said visual and audio representations indicate billing data for use of the prosthetic system.

11. The apparatus as recited in claim 7, wherein said visual and audio representations indicate alerts directing said user to check a residual limb disposed within said prosthetic socket for injuries due to excess pressure.

12. The apparatus as recited in claim 7, wherein said visual and audio representations indicate distance traveled by said prosthetic system.

13. The apparatus as recited in claim 7, wherein said visual and audio representations indicate speed of said prosthetic system in a direction traveled by said user.

14. An apparatus for use with a prosthetic system, the apparatus comprising:
a housing, completely and entirely disposed within an interior cavity of a prosthetic socket that provides also for insertion of a covered residual limb into said interior cavity, said prosthetic socket having a formed reservoir within said interior cavity inside of which said housing is disposed, wherein said housing presents a first surface for contacting a second surface of said covered residual limb when inserted into said interior cavity, said housing comprising:
a controller, that operates to gather data and derive prosthetic information from a plurality of sensors, and that transmits said prosthetic information over a wireless radio link; and
a seal, that seals said housing to said interior cavity of said prosthetic socket, and that seals a low pressure side within said prosthetic socket from an ambient environment;
a pump, wherein the pump is coupled to said controller and wherein the pump is operable to maintain a prescribed negative air pressure within said prosthetic socket; and
a wireless smart device, coupled to said controller via said wireless radio link, that receives said prosthetic information, and that provides visual and audio representations of said prosthetic information to a user.

15. The apparatus as recited in claim 14, wherein said plurality of sensors comprises:
an accelerometer, that senses relative motion data corresponding to the prosthetic system, and that provides said relative motion data to said controller, wherein said controller derives a portion of said prosthetic information based upon said relative motion data.

16. The apparatus as recited in claim 14, wherein said plurality of sensors comprises:
a Global Positioning System (GPS) receiver, that senses real time position data corresponding to the prosthetic system, and that provides said real time position data to said controller, wherein said controller derives a portion of said prosthetic information based upon said real time position data.

17. The apparatus as recited in claim 14, wherein said plurality of sensors comprises:
a temperature sensor, that senses temperature data corresponding to the prosthetic system, and that provides said temperature data to said controller, wherein said controller derives a portion of said prosthetic information based upon said temperature data.

18. The apparatus as recited in claim 14, wherein said plurality of sensors comprises:
a barometric pressure sensor, that senses pressure data corresponding to the interior of said prosthetic socket, and that provides said pressure data to said controller, wherein said controller derives a portion of said prosthetic information based upon said temperature data, and wherein said vacuum pump is actuated additionally as a function of said pressure data.

19. The apparatus as recited in claim 14, wherein said wireless radio link comprises a BLUETOOTH radio link, and wherein said smart device comprises a smart cellular telephone.

20. The apparatus as recited in claim 19, wherein said smart cellular telephone executes an application program that enables said smart cellular telephone to receive and transmit said prosthetic information, to provide said visual and audio representations, and to receive input from said user for transmission to said controller.

21. The apparatus as recited in claim 20, wherein said visual and audio representations indicate time of wear for the prosthetic system.

22. The apparatus as recited in claim 20, wherein said visual and audio representations indicate a time to remove the prosthetic system.

23. The apparatus as recited in claim 19, wherein said visual and audio representations indicate billing data for use of the prosthetic system.

24. The apparatus as recited in claim 20, wherein said visual and audio representations indicate alerts directing said user to check a residual limb disposed within said prosthetic socket for injuries due to excess pressure.

25. The apparatus as recited in claim 20, wherein said visual and audio representations indicate distance traveled by said prosthetic system.

26. The apparatus as recited in claim 20, wherein said visual and audio representations indicate speed of said prosthetic system in a direction traveled by said user.

27. An apparatus for use with a prosthetic system, the apparatus comprising:
a prosthetic socket, that provides a conforming interior receptacle for a covered residual limb of a user, said interior receptacle comprising a formed reservoir within said interior receptacle;
a housing, completely and entirely disposed in said formed reservoir of said interior receptacle, wherein said housing presents a first surface for contacting a second surface of said covered residual limb when inserted into said interior receptacle, said housing comprising:
a controller, that operates to gather data and derive prosthetic information from a plurality of sensors, and that transmits said prosthetic information over a wireless radio link, wherein said controller and said plurality of sensors are disposed within said housing; and
a seal, that seals said housing to said interior receptacle, and that that seals said interior receptacle from an ambient environment;
a pump, wherein the pump is coupled to said controller and wherein the pump is operable to maintain a prescribed negative air pressure within said prosthetic socket;
a wireless smart device, coupled to said controller via said wireless radio link, that receives said prosthetic information, and that provides visual and audio representations of said prosthetic information to said user.

28. The apparatus as recited in claim 27, wherein said plurality of sensors comprises:
an accelerometer, that senses relative motion data corresponding to the prosthetic system, and that provides said relative motion data to said controller, wherein said controller derives a portion of said prosthetic information based upon said relative motion data.

29. The apparatus as recited in claim 27, wherein said plurality of sensors comprises:
a Global Positioning System (GPS) receiver, that senses real time position data corresponding to the prosthetic system, and that provides said real time position data to said controller, wherein said controller derives a portion of said prosthetic information based upon said real time position data.

30. The apparatus as recited in claim 27, wherein said plurality of sensors comprises:
a temperature sensor, that senses temperature data corresponding to the prosthetic system, and that provides said temperature data to said controller, wherein said controller derives a portion of said prosthetic information based upon said temperature data.

31. The apparatus as recited in claim 27, wherein said plurality of sensors comprises:
a barometric pressure sensor, that senses pressure data corresponding to the interior of said prosthetic socket, and that provides said pressure data to said controller, wherein said controller derives a portion of said prosthetic information based upon said temperature data, and wherein said vacuum pump is actuated additionally as a function of said pressure data.

32. The apparatus as recited in claim 27, wherein said wireless radio link comprises a BLUETOOTH radio link, and wherein said smart device comprises a smart cellular telephone.

33. The apparatus as recited in claim 32, wherein said smart cellular telephone executes an application program that enables said smart cellular telephone to receive and transmit said prosthetic information, to provide said visual and audio representations, and to receive input from said user for transmission to said controller.

34. The apparatus as recited in claim 33, wherein said visual and audio representations indicate time of wear for the prosthetic system.

35. The apparatus as recited in claim 33, wherein said visual and audio representations indicate a time to remove the prosthetic system.

36. The apparatus as recited in claim 33, wherein said visual and audio representations indicate billing data for use of the prosthetic system.

37. The apparatus as recited in claim 33, wherein said visual and audio representations indicate alerts directing said user to check a residual limb disposed within said prosthetic socket for injuries due to excess pressure.

38. The apparatus as recited in claim 33, wherein said visual and audio representations indicate distance traveled by said prosthetic system.

39. The apparatus as recited in claim 33, wherein said visual and audio representations indicate speed of said prosthetic system in a direction traveled by said user.

40. The apparatus as recited in claim 1, wherein the pump is a vacuum pump that is dynamically actuated by said controller.

41. The apparatus as recited in claim 14, wherein the pump is a vacuum pump that is dynamically actuated by said controller.

42. The apparatus as recited in claim 27, wherein the pump is a vacuum pump wherein said vacuum pump is dynamically actuated by said controller.

* * * * *